(12) United States Patent
MacKinnon et al.

(10) Patent No.: US 7,151,601 B2
(45) Date of Patent: *Dec. 19, 2006

(54) APPARATUS AND METHODS RELATING TO WAVELENGTH CONDITIONING OF ILLUMINATION

(75) Inventors: Nicholas B. MacKinnon, Vancouver (CA); Calum E. MacAulay, Vancouver (CA); Ulrich Stange, Vancouver (CA)

(73) Assignee: Tidal Photonics, Inc., Vancouver (CA)

( * ) Notice: Subject to any disclaimer, the term of this patent is extended or adjusted under 35 U.S.C. 154(b) by 142 days.

This patent is subject to a terminal disclaimer.

(21) Appl. No.: 10/854,828

(22) Filed: May 25, 2004

(65) Prior Publication Data

US 2004/0218177 A1    Nov. 4, 2004

Related U.S. Application Data

(63) Continuation of application No. 10/061,966, filed on Jan. 31, 2002, now Pat. No. 6,781,691.

(60) Provisional application No. 60/265,991, filed on Feb. 2, 2001, provisional application No. 60/310,940, filed on Aug. 7, 2001.

(51) Int. Cl.
*G01J 3/28* (2006.01)

(52) U.S. Cl. .................................... 356/326; 356/328

(58) Field of Classification Search .................... None
See application file for complete search history.

(56) References Cited

U.S. PATENT DOCUMENTS

| | | | |
|---|---|---|---|
| 5,037,173 A | 8/1991 | Sampsell et al. | 385/17 |
| 5,090,807 A * | 2/1992 | Tai | 356/310 |
| 5,461,475 A * | 10/1995 | Lerner et al. | 356/300 |
| 5,796,508 A * | 8/1998 | Suzuki | 359/224 |
| 5,828,485 A | 10/1998 | Hewlett | 359/291 |
| 5,938,319 A | 8/1999 | Hege | 362/459 |
| 6,046,808 A | 4/2000 | Fateley | 356/330 |
| 6,128,077 A * | 10/2000 | Jovin et al. | 356/310 |
| 6,128,078 A | 10/2000 | Fateley | 356/330 |
| 6,412,972 B1 * | 7/2002 | Pujol et al. | 362/272 |
| 6,710,909 B1 * | 3/2004 | Naito | 359/291 |
| 6,882,770 B1 * | 4/2005 | Neilson et al. | 385/18 |
| 6,900,825 B1 * | 5/2005 | Kito | 347/239 |
| 6,996,292 B1 * | 2/2006 | Gentry et al. | 382/281 |
| 2002/0057431 A1 | 5/2002 | Fateley et al. | 356/330 |
| 2002/0176151 A1 | 11/2002 | Moon et al. | 359/298 |

FOREIGN PATENT DOCUMENTS

WO     WO 98/52386     11/1998

* cited by examiner

*Primary Examiner*—Layla G. Lauchman
*Assistant Examiner*—Juan D. Valentin, II
(74) *Attorney, Agent, or Firm*—Graybeal Jackson Haley LLP

(57) ABSTRACT

Lighting systems comprising a spectrum former upstream from a reflective pixelated spatial light modulator (reflective SLM), the SLM reflecting substantially all of the light in the spectrum into at least two different light paths, that do not reflect back to the light source or the spectrum former. At least one of the light paths acts as a projection light path and transmits desired light out of the lighting system. The lighting systems provide virtually any desired color(s) and intensity(s) of light, and avoid overheating problems by deflecting unwanted light and other electromagnetic radiation out of the system or to a heat management system. The systems can be part of another system, a luminaire, or any other suitable light source. The systems can provide virtually any desired light, from the light seen at the break of morning to specialized light for treating cancer or psoriasis, and may change color and intensity at speeds that are perceptually instantaneous.

56 Claims, 3 Drawing Sheets

CASE 1 – NO SPECTRAL CONDITIONING

CASE 2 – SPECTRAL CONDITIONING TO SIMULATE OUTPUT LIGHT FROM A CRT

XENON LIGHT

XENON LIGHT

LIGHT SOURCE SPECTRUM

ALL DMD MIRRORS

WHITE CRT

DMD MIRROR PATTERN

OUTPUT LIGHT

OUTPUT LIGHT

OUTPUT SPECTRUM

APPARATUS AND METHODS RELATING TO WAVELENGTH CONDITIONING OF ILLUMINATION

CROSS-REFERENCE TO RELATED APPLICATIONS

The present application is a continuation of U.S. patent application Ser. No. 10/061,966, filed Jan. 31, 2002, now U.S. Pat. No. 6,781,691, which application claims priority from U.S. provisional patent application No. 60/265,991, filed Feb. 2, 2001, and from U.S. provisional patent application No. 60/310,940, filed Aug. 7, 2001.

BACKGROUND

Light bulbs usually provide light that includes all the colors in the rainbow: violet, blue, green, yellow, orange, and red. When all of these colors are present, the light is known as "white light." The rainbow, which is the separated colors, is known as a spectrum. Different kinds of light bulbs provide different quantities of the various colors, which means, for example, that some light bulbs provide more red light than blue light, while other light bulbs provide more green light than orange light. In addition, most light bulbs also provide light that is not visible to the naked eye, such as ultraviolet (UV) light and infrared (IR) light.

The different colors of light are known as different wavelengths of light, and range in the visible spectrum from violet or blue light having a wavelength of about 400 nm to red light having a wavelength of about 700 nm; UV light is typically between about 300 nm to 400 nm, and IR light is typically from about 700 nm to 1000 nm.

For a long time, people have wanted to select specific wavelengths and/or intensities of light for specific situations, such as for lighting a movie scene so that it looks like the middle of a bright summer day in Mexico City or a cool fall evening with a beautiful sunset in Anchorage, Ak., for diagnosing or treating disease, for measuring or analyzing the chemical or physical properties of an object, or for initiating a physical or chemical change in an object or compound or organism.

In order to obtain particular wavelengths and intensities of light, movie sets employ highly skilled and specialized lighting technicians that use very expensive light bulbs, lighting apparatus, lighting filters (such as colored "gels"), and the like. The intense heat generated by the lights, however, reaches oven-like temperatures and can cook film, filters, and lighting elements. Other situations likewise employ expensive personnel and apparatus.

In some previous attempts to deal with these problems, a spectrum former, such as a prism, has been placed in front of the light bulb to separate the light beam into its respective wavelengths, then a transmissive pixelated spatial light modulator has been placed in the spectrum. A pixelated spatial light modulator is typically a square or rectangular device (although other shapes are possible) that contains a large number of tiny pixels and can be turned on or off at will. Turning a line of pixels "on" while turning all others "off" permits the spatial light modulator to pick a specific color of light; more complex on/off patterns can pick more complex wavelength and intensity distributions. However, these prior attempts have been problematic because the pixelated spatial light modulators have either absorbed the undesired light or reflected it back to the original light source or spectrum former. In either case, the heat from the undesired light is not dissipated and serious problems may ensue.

Thus, there has gone unmet a need for lighting systems and luminaires that provide selected light wavelengths and intensities but that do not overheat, and that can also rapidly switch between different selected wavelengths or intensities, including highly complex groupings of wavelengths or intensities. The present invention provides these and other advantages.

SUMMARY

The present invention provides lighting systems that provide virtually any desired color(s) and intensity(s) of light, from white light to light containing only a certain color(s) and intensity(s). The colors, or "spectral output," which means a particular wavelength, band of wavelengths, or set of wavelengths, as well as the intensities, which means a "wavelength dependent intensity distribution," can be combined and varied as desired. The lighting systems avoid overheating problems and can be part of other systems or stand alone units such as luminaires (for example, the high-output lighting units used to illuminate movie scenes, concert stages, and night-time construction sites). The systems can provide any desired light, such as UV light, visible light, and infrared light.

The lighting systems are a low cost, effective approach to providing carefully controlled light for a variety of purposes such as medicine, movies, theater, photography, and sports. For example, the light can be selected to substantially mimic light such as high noon in New York City, or the light necessary to diagnose or treat cancer. Additionally, the lighting can be rapidly switched from one desired scenario to another without moving major parts of the system.

The lighting systems typically comprise a spectrum former upstream from a reflective pixelated spatial light modulator (SLM). The spectrum former accepts a light beam from a light source and turns it into a spectrum, and the spectrum is then transmitted to the SLM, such as a digital micromirror device (DMD). The SLM reflects substantially all of the light impinging on the SLM into at least two different light paths that do not reflect back to the light source or the spectrum former. At least one of the light paths acts as a projection light path and transmits desired light out of the lighting system or luminaire. The other light path can act as a repository for the reflected energy, an alternate projection light path, and/or a detection light path wherein a detector measures the light reflected from the pixelated SLM to determine whether the light has the desired wavelength and intensity characteristics. Because the mirrors in the pixelated SLM can be rapidly switched back and forth between different light paths, the reflected light beam that contains the desired wavelength and intensity distribution(s) can be alternated back and forth between a projection light path and detection light path. If desired, one or more additional pixelated spatial light modulators can be provided in one or more of the light paths, to provide further enhanced specificity and preciseness in the wavelength and intensity distributions or other added benefits.

The pixelated SLM may be operably connected to a controller, which controller contains computer-implemented programming that controls the on/off pattern of the pixels in the pixelated SLM. The controller can be located in any desired location to the rest of the system. For example, the controller can be either within a housing of the luminaire or it can be located remotely, connected by a wire, cellular link or radio link to the rest of the system. If desired, the controller, which is typically a single computer but can be a plurality of linked computers, a plurality of unlinked computers, computer chips separate from a full computer or other suitable controller devices, can also contain one or more computer-implemented programs that provide specific lighting characteristics, i.e., specific desired, selected spectral outputs and wavelength dependent intensities, corresponding to known light sources such as commercial light sources, specific natural lighting situations, such as afternoon at a particular longitude, latitude, time of day and cloudiness, or a specific light for disease diagnosis or treatment, or to invoke disease treatment (for example by activating a drug injected into a tumor in an inactive form), or other particular situations.

In one aspect, the present invention provides a lighting system that provides a variable selected spectral output and a variable wavelength dependent intensity distribution. The lighting system comprising a light path that comprises: a) a spectrum former able to provide a spectrum from a light beam traveling along the light path, and b) a reflective pixelated spatial light modulator located downstream from and optically connected to the spectrum former, the reflective pixelated spatial light modulator reflecting substantially all light impinging on the reflective pixelated spatial light modulator and switchable to reflect light from the light beam between at least first and second reflected light paths that do not reflect back to the spectrum former. The reflective pixelated spatial light modulator can be a digital micromirror device. The reflective pixelated spatial light modulator is operably connected to at least one controller containing computer-implemented programming that controls an on/off pattern of pixels in the reflective pixelated spatial light modulator to reflect a desired segment of light in the spectrum to the first reflected light path and reflect substantially all other light in the spectrum impinging on the reflective pixelated spatial light modulator to at least one of the second reflected light path and another reflected light path that does not reflect back to the spectrum former, the desired segment of light consisting essentially of a desired selected spectral output and a desired wavelength dependent intensity distribution.

In some embodiments, the system further comprises a light source located upstream from the spectrum former, and the spectrum former comprises at least one of a prism and a diffraction grating, which can be a reflective diffraction grating, transmission diffraction grating, variable wavelength optical filter, or a mosaic optical filter. The system may or may not comprise, between the spectrum former and the reflective pixelated spatial light modulator, an enhancing optical element that provides a substantially enhanced image of the spectrum from the spectrum former to the reflective pixelated spatial light modulator. The reflective pixelated spatial light modulator can be a first reflective pixelated spatial light modulator, and the desired segment of light can be directed to a second reflective pixelated spatial light modulator operably connected to the same controller or another controller containing computer-implemented programming that controls an on/off pattern of pixels in the second reflective pixelated spatial light modulator to reflect the desired segment or other segment of light in one direction and reflect other light in the spectrum in at least one other direction. The system can further comprise an optical projection device located downstream from the first reflective pixelated spatial light modulator to project light out of the lighting system as a directed light beam.

The desired segment of light can be selected to substantially mimic a spectral output and a wavelength dependent intensity distribution of at least one of a known lamp, a cathode ray tube image display device, a light emissive image display device, firelight, candlelight, sunlight or other desired natural ambient lighting scenarios, the output energy for disease treatment, photodynamic therapy, or disease diagnosis, or to enhance contrast for detection or discrimination of a desired object in a scene.

In another aspect, the present invention provides a stand alone luminaire sized to project light onto a scene and having a variable selected spectral output and wavelength dependent intensity distribution. The luminaire can comprise a) a high output light source, b) a spectrum former optically connected to and downstream from the light source to provide a spectrum from a light beam emitted from the light source, c) an enhancing optical element connected to and downstream from the spectrum former that provides an enhanced image of the spectrum; d) a reflective pixelated spatial light modulator located downstream from and optically connected to the spectrum former, the reflective pixelated spatial light modulator reflecting substantially all light impinging on the reflective pixelated spatial light modulator and switchable between at least first and second reflected light paths that do not reflect back to the spectrum former, wherein the reflective pixelated spatial light modulator can be operably connected to at least one controller containing computer-implemented programming that controls an on/off pattern of pixels in the reflective pixelated spatial light modulator to reflect a desired segment of light in the spectrum in first reflected light path and reflect other light in the spectrum to at least one of the second reflected light path and another reflected light path that does not reflect back to the spectrum former, the desired segment of light consisting essentially of a desired selected spectral output and a desired wavelength dependent intensity distribution; and, e) a projection system optically connected to and downstream from the reflective pixelated spatial light modulator in the first direction, wherein the projection system projects the desired segment as a directed light beam to illuminate the scene.

The luminaire can further comprise a detector optically connected to and downstream from the reflective pixelated spatial light modulator, the detector also operably connected to a controller containing computer-implemented programming able to determine from the detector whether the desired segment contains a desired selected spectral output and a desired wavelength dependent intensity distribution, and adjust the on/off pattern of pixels in the reflective pixelated spatial light modulator to improve the correspondence between the desired segment and the desired selected spectral output and the desired wavelength dependent intensity distribution. The luminaire can also comprise a heat removal element operably connected to the light source to remove undesired energy emitted from the light source toward at least one of the reflective pixelated spatial light modulator, the enhancing optical element, and the spectrum former. The luminaires and lighting systems, as well as methods, kits, and the like related to them, can further comprise various elements that may be specifically discussed for only one or the other (for example, the detector of the luminaire is also suitable for use with the lighting system).

The heat removal element can be located between the spectrum former and the first reflective spatial light modulator, between the lamp and the spectrum former, or elsewhere as desired. The heat removal element can comprise a dichroic mirror. The dichroic mirror can transmits desired wavelengths and reflects undesired wavelengths, or vice-versa. The undesired energy can be directed to an energy absorbing surface and thermally conducted to a radiator. The heat removal element can be an optical cell containing a liquid that absorbs undesired wavelengths and transmits desired wavelengths. The liquid can be substantially water and can flow through the optical cell via an inlet port and outlet port in a recirculating path between the optical cell and a reservoir. The recirculating path and the reservoir can comprise a cooling device, which can be a refrigeration unit, a thermo-electric cooler, or a heat exchanger.

The luminaire further can comprise a spectral recombiner optically connected to and located downstream from the pixelated spatial light modulator, which can comprise a prism, a Lambertian optical diffusing element, a directional light diffuser such as a holographic optical diffusing element, a lenslet array, or a rectangular light pipe. In one embodiment, the spectral recombiner can comprise an operable combination of a light pipe and at least one of a lenslet array and a holographic optical diffusing element. The detector can be located in the at least one other direction, and can comprise at least one of a CCD, a CID, a CMOS, and a photodiode array. The high output light source, the spectrum former, the enhancing optical element that provides an enhanced image, the reflective pixelated spatial light modulator, and the projection system, can all be located in a single housing, or fewer or more elements can be located in a single housing.

In a further aspect, the present invention provides methods of lighting a scene comprising: a) directing a light beam along a light path and through a spectrum former to provide a spectrum from the light beam traveling; b) reflecting the spectrum off a reflective pixelated spatial light modulator that can be operably connected to at least one controller containing computer-implemented programming that controls an on/off pattern of pixels in the reflective pixelated spatial light modulator, wherein the reflecting can comprise reflecting a desired segment of light in the spectrum in a first reflected light path that can be not back to the spectrum former and reflecting substantially all other light in the spectrum impinging on the reflective pixelated spatial light modulator in at least one second reflected light path that can be not back to the spectrum former, to provide a modified light beam consisting essentially of a selected spectral output and a selected wavelength dependent intensity distribution.

The methods further can comprise emitting the light beam from a light source located in a same housing as and upstream from the spectrum former. The methods further can comprise switching the modified light beam between the first reflected light path and the second reflected light path. The methods further can comprise passing the light beam by an enhancing optical element between the spectrum former and the reflective pixelated spatial light modulator to provide a substantially enhanced image of the spectrum from the spectrum former to the reflective pixelated spatial light modulator. The reflective pixelated spatial light modulator can be a first reflective pixelated spatial light modulator, and the methods further can comprise reflecting the modified light beam off a second reflective pixelated spatial light modulator operably connected to at least one controller containing computer-implemented programming that controls an on/off pattern of pixels in the second reflective pixelated spatial light modulator to reflect the desired segment of light in one direction and reflect other light in the spectrum in at least one other direction.

The methods further can comprise passing the modified light beam by an optical projection device located downstream from at least one of the first reflective pixelated spatial light modulator and the second reflective pixelated spatial light modulator to project light as a directed light beam.

The methods of lighting a scene can also comprise: a) directing a light beam along a light path and through a spectrum former to provide a spectrum from the light beam traveling; and, b) passing the spectrum via a pixelated spatial light modulator located downstream from and optically connected to the spectrum former, the pixelated spatial light modulator operably connected to at least one controller containing computer-implemented programming that controls an on/off pattern of pixels in the pixelated spatial light modulator, wherein the on/off pattern can be set to pass a desired segment of light in the spectrum in one direction and interrupt other light in the spectrum impinging on the pixelated spatial light modulator, to provide a modified light beam consisting essentially of a selected spectral output and a selected wavelength dependent intensity distribution, and wherein the methods does not comprise passing the spectrum by an enhancing optical element between the spectrum former and the pixelated spatial light modulator that provides an enhanced image of the spectrum from the spectrum former to the pixelated spatial light modulator.

In still other aspects, the present invention provides methods of emitting modified light consisting essentially of a desired selected spectral output and a desired wavelength dependent intensity distribution from a stand alone luminaire. The methods can comprise: a) emitting light from a high output light source located in a housing of the luminaire; b) passing the light by a spectrum former optically connected to and downstream from the light source to provide a spectrum from a light beam emitted from the light source; c) passing the spectrum by an enhancing optical element connected to and downstream from the spectrum former to provide an enhanced image of the spectrum; d) reflecting the spectrum off a reflective pixelated spatial light modulator that can be operably connected to at least one controller containing computer-implemented programming that controls an on/off pattern of pixels in the reflective pixelated spatial light modulator, wherein the reflecting can comprise reflecting a desired segment of light in the spectrum in a first reflected light path that can be not back to the spectrum former and reflecting substantially all other light in the spectrum impinging on the reflective pixelated spatial light modulator in at least one second reflected light path that can be not back to the spectrum former, to provide a modified light beam consisting essentially of a selected spectral output and a selected wavelength dependent intensity distribution; and, e) passing the modified light beam by a projection system optically connected to and downstream from the reflective pixelated spatial light modulator in the first direction, wherein the projection system projects the modified light beam from the luminaire as a directed light beam.

The methods can further comprise reflecting the desired segment of light to a detector optically connected to and downstream from the reflective pixelated spatial light modulator, the detector located in the second reflected light path or otherwise as desired and operably connected to the controller, wherein the controller contains computer-implemented programming able to determine from the detector whether the desired segment contains the desired selected spectral output and the desired wavelength dependent intensity distribution, and therefrom determining whether the first segment contains the desired selected spectral output and the desired wavelength dependent intensity distribution. The methods can comprise adjusting the on/off pattern of pixels in the reflective pixelated spatial light modulator to improve the correspondence between the desired segment and the desired selected spectral output and the desired wavelength dependent intensity distribution.

The methods can also comprise removing undesired energy emitted from the light source toward at least one of the reflective pixelated spatial light modulator, the enhancing optical element, and the spectrum former, the removing effected via a heat removal element operably connected to the light source. The methods further can comprise a spectral recombiner optically connected to and located downstream from the reflective pixelated spatial light modulator.

These and other aspects, features and embodiments are set forth within this application, including the following Detailed Description and attached drawings. The present invention comprises a variety of aspects, features, and embodiments; such multiple aspects, features and embodiments can be combined and permuted in any desired manner. In addition, various references are set forth herein, including in the Cross-Reference To Related Applications, that discuss certain apparatus, systems, methods, or other information; all such references are incorporated herein by reference in their entirety and for all their teachings and disclosures, regardless of where the references may appear in this application.

DETAILED DESCRIPTION

Figure 1:
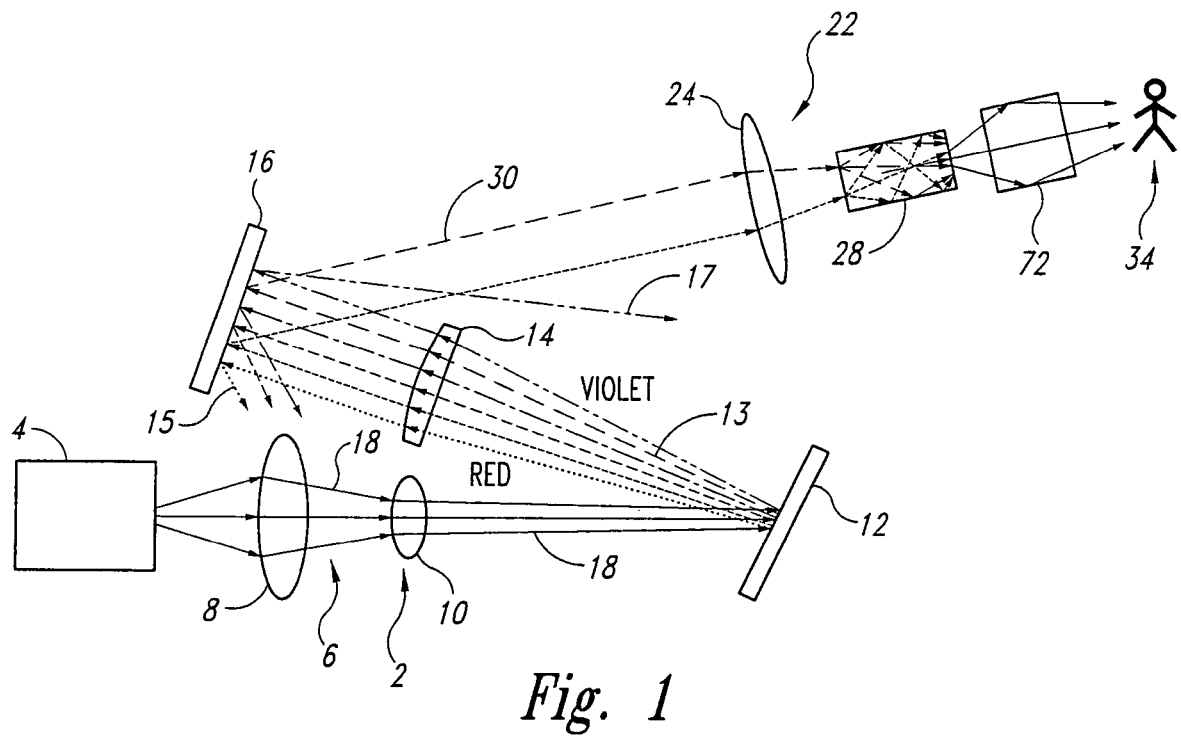
FIG. 1 provides a schematic depiction of a lighting system according to an embodiment comprising a single pixelated SLM.

The present invention comprises lighting systems comprising a spectrum former upstream from a reflective pixelated spatial light modulator (SLM), the SLM reflecting substantially all of the light in the spectrum into at least two different light paths, none of which reflect back to the light source or the spectrum former. At least one of the light paths acts as a projection light path and transmits desired light out of the lighting system. The lighting systems provide virtually any desired color(s) and intensity(s) of light, and avoid overheating problems by deflecting unwanted light and other electromagnetic radiation—and therefore unwanted heat—out of the system or to a heat management system. Thus, the heat is removed from the optical elements of the system. The systems can be part of another system, a luminaire, or any other suitable light source. The systems can provide virtually any desired light, from the light seen at the break of morning to specialized light for treating cancer or psoriasis, and may change color and intensity at speeds that are perceptually instantaneous, for example in less than a millisecond.

Turning to some general information about light, the energy distribution of light is what determines the nature of its interaction with an object, compound or organism. A common way to determine the energy distribution of light is to measure the amount or intensity of light at various wavelengths to determine the energy distribution or spectrum of the light. To make light from a light source useful for a particular purpose it can be conditioned to remove undesirable wavelengths or intensities, or to enhance the relative amount of desirable wavelengths or intensities of light.

A high signal to noise ratio and high out of band rejection enhances the simulation of the spectral characteristics of different light sources or lighting environments, and also enhances fluorescence excitation, spectroscopy or clinical treatments such as photodynamic therapy.

The systems and methods, including kits and the like comprising the systems or for making or implementing the systems or methods, provide the ability to selectively, and variably, decide which colors, or wavelengths, from a light source will be projected from the system, and how strong each of the wavelengths will be. The wavelengths can be a single wavelength, a single band of wavelengths, a group of wavelengths/wavelength bands, or all the wavelengths in a light beam. If the light comprises a group of wavelengths/wavelengths bands, the group can be either continuous or discontinuous. The wavelengths can be attenuated so that the relative level of one wavelength to another can be increased or decreased (e.g., decreasing the intensity of one wavelength among a group of wavelengths effectively increases the other wavelengths relative to the decreased wavelength). This is highly advantageous because such fine control of spectral output and wavelength dependant intensity distribution permits a single lighting system to provide highly specialized light such as light for diagnosing or treating disease or activating drugs, as well the ability to substantially mimic desirable lighting conditions such as a known lamp, a cathode ray tube image display device, a light emissive image display device, a desired natural ambient lighting scenario such as light at a specific longitude, latitude and weather condition, firelight, candlelight, or sunlight, or other sources of optical radiation.

Definitions.

The following paragraphs provide definitions of some of the terms used herein. All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

A "controller" is a device that is capable of controlling a spatial light modulator, a detector or other elements of the apparatus and methods herein. A "controller" contains or is linked to computer-implemented programming. Typically, a controller comprises one or more computers or other devices comprising a central processing unit (CPU) and directs other devices to perform certain functions or actions, such as the on/off pattern of the pixels in the pixelated SLM, the on/off status of pixels of a pixelated light detector (such as a charge coupled device (CCD) or charge injection device (CID)), and/or compile data obtained from the detector, including using such data to make or reconstruct images or as feedback to control an upstream spatial light modulator. A computer comprises an electronic device that can store coded data and can be set or programmed to perform mathematical or logical operations at high speed. Controllers are well known in the art and selection of a desirable controller for a particular aspect of the present invention is within the scope of the art in view of the present disclosure.

A "spatial light modulator" (SLM) is a device that is able to selectively modulate light. The present invention comprises one or more spatial light modulators disposed in the light path of an illumination system. A pixelated spatial light modulator comprises an array of individual pixels, which are a plurality of spots that have light passing characteristics such that they transmit, reflect or otherwise send light along a light path, or instead block the light and prevent it or interrupt it from continuing along the light path. Such pixelated arrays are well known in the art, having also been referred to as a multiple pattern aperture array, and can be formed by an array of ferroelectric liquid crystal devices, electrophoretic displays, or by electrostatic microshutters. See, U.S. Pat. Nos. 5,587,832; 5,121,239; R. Vuelleumier, Novel Electromechanical Microshutter Display Device, Proc. Eurodisplay '84, Display Research Conference September 1984.

A reflective pixelated SLM comprises an array of highly reflective mirrors that are switchable been at least two different angles of reflection. One example of a reflective pixelated SLM is a digital micromirror device (DMD), as well as other MicroElectroMechanical Structures (MEMS). DMDs can be obtained from Texas Instruments, Inc., Dallas, Tex., U.S.A. In this embodiment, the mirrors have three states. In a parked or "0" state, the mirrors parallel the plane of the array, reflecting orthogonal light straight back from the array. In one energized state, or a "−10" state, the mirrors fix at −10° relative to the plane of the array. In a second energized state, or a "+10" state, the mirrors fix at +10° relative to the plane of the array. When a mirror is in the "on" position light that strikes that mirror is directed into the projection light path. When the mirror is in the "off" position light is directed away from the projection light path. On and off can be selected to correspond to energized or non-energized states, or on and off can be selected to correspond to different energized states. If desired, the light directed away from the projection light path can also be collected and used for any desired purpose (in other words, the DMD can simultaneously cr serially provide two or more useful light paths). The pattern in the DMD can be configured to produce two or more spectral and intensity distributions simultaneously or serially, and different portions of the DMD can be used to project or image along two or more different projection light paths.

An "illumination light path" is the light path from a light source to a target or scene, while a "detection light path" is the light path for light emanating to a detector. The light includes ultraviolet (UV) light, blue light, visible light, near-infrared (NIR) light and infrared (IR) light.

"Upstream" and "downstream" are used in their traditional sense wherein upstream indicates that a given device is closer to a light source, while downstream indicates that a given object is farther away from a light source.

The scope of the present invention includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Turning to the figures, FIG. 1 schematically depicts a lighting system 2 that provides light having a variable, selected spectral output and a variable, selected wavelength dependant intensity distribution. Light source 4 is disposed at an upstream end of a light path and emits a light beam 18 that passes by an enhancing optical element 6 comprising a focusing lens 8 and a collimating lens 10. In the embodiment shown, the elements of enhancing optical element 6 are lenses that transmit the light. Any suitable optical elements that can be employed, such as lenses, mirrors, filters for the forming, mixing, imaging, collimating or other conditioning of the light that is desired. Thus, the light is passed by the enhancing optical element 6 either by transmitting the light or by reflecting the light or otherwise by acting upon the light. If desired, detectors, heat management systems and other desired elements can also be provided in the primary projection light path, connected by mirrors, lenses or other optical components. However, it is an advantage of the present system that such components need not be placed in the primary light path unless specifically desired, thereby reducing the noise and interference introduced by the additional components.

Light beam 18 continues along the light path to spectrum former 12. Spectrum former 12 can be any desired optical element that separates a light beam into its respective spectral components, such as a prism, a diffraction grating, either planar or curved, such as a reflective diffraction grating or a transmission diffraction grating, an optical filter comprising a linearly variable wavelength filter or other spatially variable wavelength filter, or a mosaic optical filter. A linearly variable wavelength filter is an optical filter where the wavelength that is transmitted varies across the face of the filter, such as filters made by OCLI, a JDS Uniphase company, where the wavelength of transmission varies in a continuous manner between positions of incident light from one end of the filter to the other end. This filter can be linearly variable, non-linearly variable or step-wise variable. After light beam 18 passes by spectrum former 12, it continues along the light path as spectrum 13. In FIG. 1, red light is depicted at the lower edge of spectrum 13 while violet light is depicted at the upper edge of spectrum 13. As depicted, spectrum 13 passes by collimating or focusing optics 14 and then on to a reflective pixelated SLM 16.

In most embodiments, the spatial light modulator is a reflective spatial light modulator, not a transmissive spatial modulator such as an LCD or liquid electrophoretic spatial light modulator. In addition, the reflective pixelated SLMs are capable of reflecting the light in a plurality of directions, and, as depicted in FIG. 1 and elsewhere herein, are located or disposed so as to not reflect light back toward either the spectrum former 12 or the light source 4. For example, the light can be directed in second reflective light path 15, or, in the embodiment shown, in a third reflective light path 17. This provides a significant vantage because it dissipates heat and other energy accompanying the spectrum, such as heat from undesired wavelengths in the spectrum, heat from additional electromagnetic radiation outside of the spectrum, and other undesired energy. If desired, the spectrum can be selected from among electromagnetic radiation outside of the visible light range, although typically the electromagnetic radiation will be selected from among wavelengths that are in or near the visible light range (usually ranging from UV light to IR light). The reflective pixelated SLM 16 can be switched from one light path to another as desired.

Reflective pixelated SLM 16 is located downstream from and is optically connected to spectrum former 12, which means that reflective pixelated SLM 16 receives a substantial portion of the spectrum, at least enough of the spectrum to act on it to provide a desired segment of light containing the desired wavelengths and wavelength intensities. Thus, the reflective pixelated SLM reflects substantially all light impinging on it. Accordingly, reflective pixelated SLM 16 provides a desired segment 30 comprising a spectrally selected light beam. Desired segment 30 then passes by a light projection optical system 22 which as depicted in FIG. 1 comprises a lens 24 and spatial mixing optics 28 and a projection lens or optical system 72 for projection to a target scene 34.

The second, or more, light paths can serve to exhaust unwanted energy, to provide alternate projection light paths, to provide detection light paths so that sampling of either the undesired light or the desired light can be obtained (the desired segment can be sampled because the on/off status of the pixels in the projection light path can be set to send the desired segment to the detector for analysis, then switched back to the projection light path). As depicted for the luminaire in FIG. 4, SLM 16 is operably connected to at least one controller 44 that contains computer-implemented programming that controls the on/off pattern of the pixels. The pattern is set to reflect the desired segment 30 of the spectrum in the first reflective light path (in FIG. 1, the first reflective light path is the same as the projection light path) and then to reflect substantially all other light in the spectrum in at least one other reflective light path. The desired segment of light then consists essentially of a desired selected spectral output and a desired wavelength dependant intensity distribution. The desired segment can be set to include any desired interference or noise light coming either intentionally, from inadequacies in the system such as background noise, or from malfunctions in the system.

Figure 2:
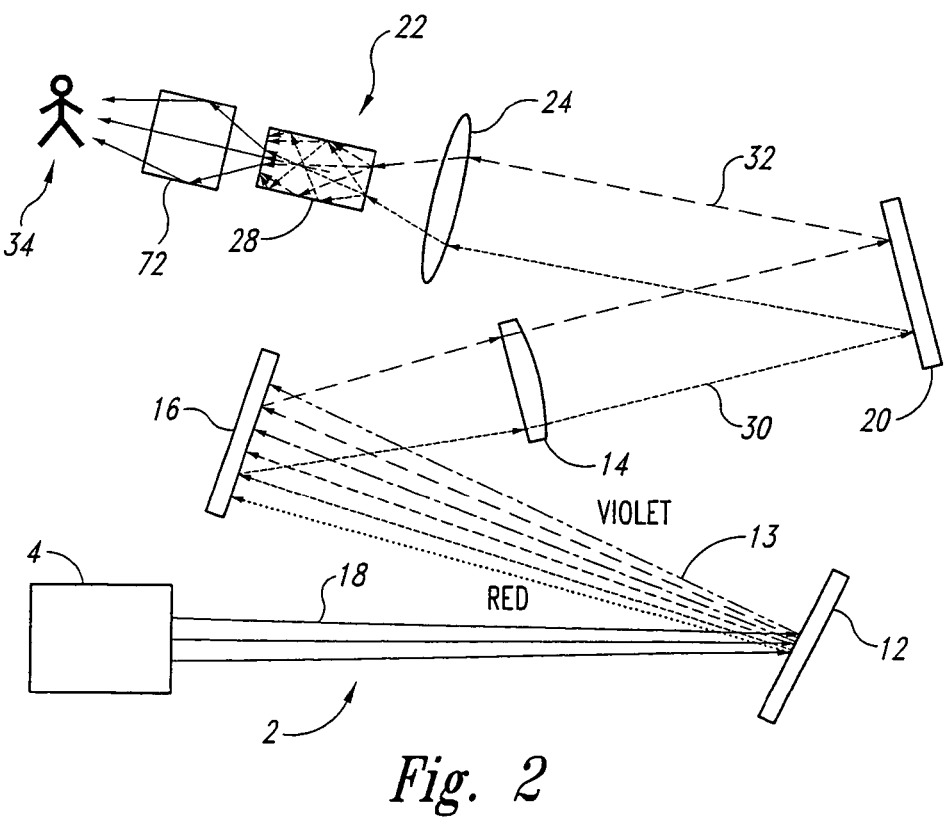
FIG. 2 provides a schematic depiction of a lighting system according to an embodiment comprising two pixelated SLMs.

FIG. 2 schematically depicts a lighting system 2 according to another embodiment. Light source 4 emits light beam 18 that passes by spectrum former 12 to provide a spectrum 13. In the embodiment in FIG. 2, the system does not comprise any enhancing optical element(s) such as lenses, mirrors and the like between either the spectrum former and the reflective pixelated SLM, or between the light source and the spectrum former. Enhancing optical elements such as lenses, mirrors, and the like, provide a substantially enhanced image of the spectrum to the reflective pixelated SLM, which means that the spectrum has not been focused or otherwise substantially improved by optical elements. In FIG. 2, spectrum 13 is reflected off reflective pixelated SLM 16 to provide desired segment 30, then passes by collimating optics 14 and reflects off a second reflective pixelated SLM 20. Second reflective pixelated SLM 20 can be set to have an on/off pattern substantially similar or identical to the pattern in the first reflective pixelated SLM 16, or otherwise as desired. Although the additional reflection and additional optical elements that may be employed may attenuate the overall power of the light beam, the non-desired light is significantly greater attenuated, and thus a very high resolution, high contrast, spectrally selected beam 32 is provided. This beam can then projected out to a target 34.

Figure 3:
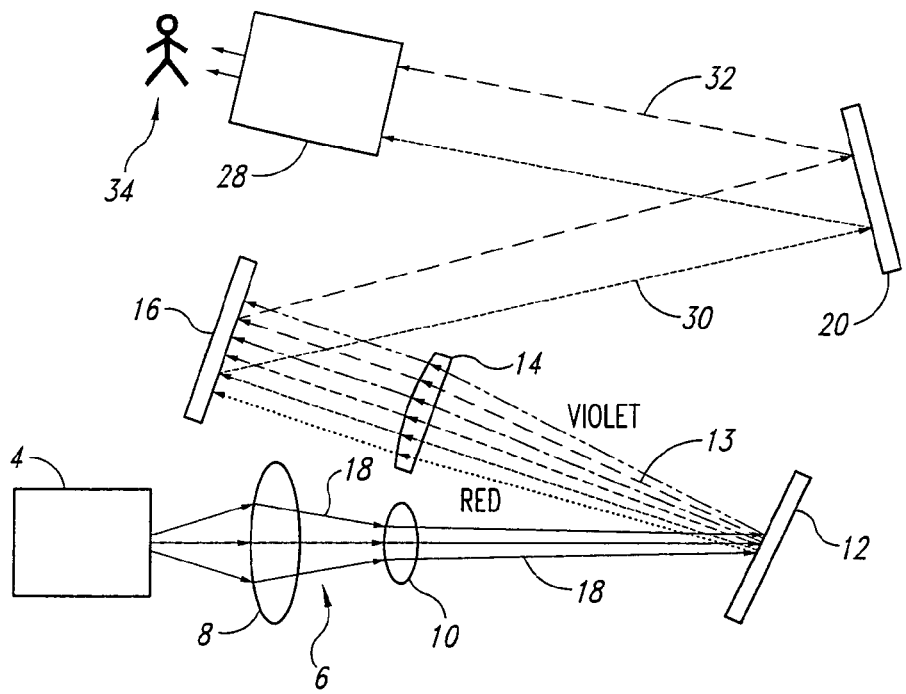
FIG. 3 provides a schematic depiction of a lighting system according to an embodiment comprising two pixelated SLMs.

FIG. 3 is similar to FIG. 2 except that certain collimating, focusing and other enhancing optical elements such as elements 6, 8, 10, 14 are disposed in light beam 18 and spectrum 13, and the system further comprises spatial mixing optics 28 that act as an optical projection device to project light out of the lighting system as a directed light beam.

Figure 4:
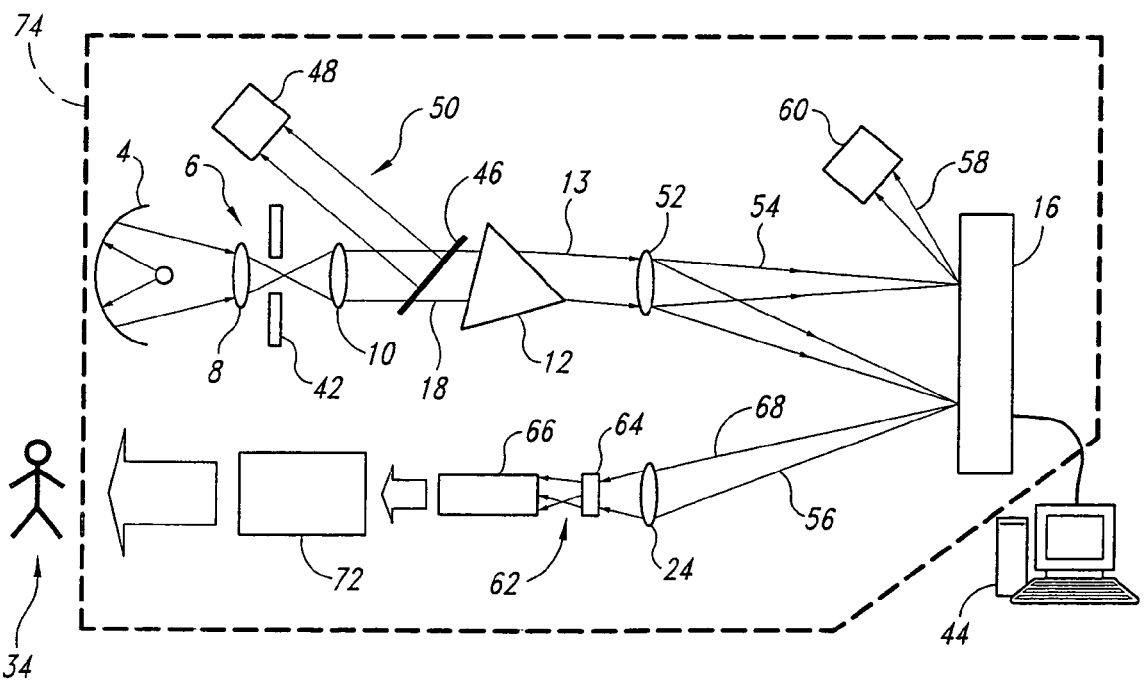
FIG. 4 is a schematic representation of a luminaire comprising a single pixelated SLM, heat management system and a detector.

FIG. 4 schematically depicts a stand-alone luminaire 40. A stand-alone luminaire is a lighting device that is mobile and portable, and typically pointable. In some embodiments, it is an advantage of the present luminaires that the light beam from the luminaire can be pointed in different directions without moving the housing 70 of the luminaire 40. A stand-alone luminaire is not merely a part of a larger device, for example it is not a light source in a movie projector, but is rather a stand-alone light source such as a spotlight, flashlight or other independent light source. The stand-alone luminaire is sized to project light onto a scene and thus comprises a high output light source, which indicates a light source of greater size and intensity (and, therefore, typically greater heat), than a light source that would be used in a small scientific instrument such as a spectrometer or spectroradiometer.

In FIG. 4, light source 4 emits light that passes by a focusing lens 8, through an aperture 42 and by collimating lens 10. Light beam 18 then impinges on a heat management system 50. In the embodiment shown, heat management system 50 comprises a heat trap 48 and a beam splitter 46 that eliminates unwanted energy from light beam 18. Heat management systems can be located in other desired locations in the luminaire (as with the lighting systems discussed elsewhere herein), for example in one direction or another of the reflected light paths emanating from the reflective SLM 16. Thus, heat management system 50 removes undesired energy emitted from the light source toward at least one of reflective pixelated SLM 16, the enhancing optical element 6, and spectrum former 12. The beam splitter 46 is typically a dichroic mirror and the system can be designed such that the dichroic mirror transmits desired wavelengths and reflects undesired wavelengths or vice-versa. The heat trap 48 can be any suitable heat trap, such as an energy absorbing surface, preferably one thermally connected to thermally conduct the heat to a radiator, or an optical cell containing a liquid that absorbs undesired wavelengths and transmits desired wavelengths, such as water. For embodiments where the heat trap 48 comprises an optical cell, the optical cell can also comprise an inlet port and an outlet port so that fresh liquid can be provided, and if desired the liquid can flow in a recirculating path between the optical cell and a reservoir. The re-circulating path or the reservoir can further comprise a cooling device such as a refrigeration unit, a thermal-electric cooler and a heat exchanger.

In FIG. 4, The collimated light passing the heat trap is directed to wavelength dispersing element 12. The wavelength dispersed beam passing this element comprises a group of wavelengths, where any given wavelength in the beam travels a path that is substantially parallel to similar wavelengths but varies in angle relative to the optical axis of the system, with respect to other wavelengths. Wavelength dispersed beam 13 passes by a light focusing lens 52 that focuses the wavelength dispersed beam into a spread spectrum 54 on the surface of SLM 16. Spread spectrum 54 then reflects off reflective pixelated SLM 16 in either a first direction 56 or in a second direction 58. Reflective pixelated SLM 16 is operably connected to a controller 44. Additional directions or light paths can be provided if desired. In second direction 58, the light is directed to a spectral measuring device 60. Such spectral measuring devices are well known in the art and can comprise, for example, spectrometers, spectroradiometers, charge coupled devices (CCDs), charge injection devices (CIDs), a complementary metal-oxide semi-conductors (CMOSs), photodiode arrays, or any other desired spectral measuring devices. As discussed elsewhere, the spectral measuring device 60 provides analysis and determination whether either desired segment or any other portion of the spectrum 54 comprises the desired wavelength (s) and intensity(s).

Spectrally selected beam 68, which comprises the desired segment of light, passes to a light mixing system 62, which in the embodiment shown comprises a spectral recombiner comprising a directional diffuser, such as a holographic optical diffuser 64 and a light pipe 66. The spectrally selected beam 68 then passes by a projection system 72 suitable for projecting the light to a scene. The light exits the luminaire via a passageway 74 in a single housing 70 that contains the elements of luminaire 40. Typically, the housing contains at least the light source 4, the spectrum former 12, at least a portion of the heat management system 50, the reflective pixelated SLM 16, and the various optical systems such as 6, 62, and 72. If desired, the housing can contain all of the elements for the luminaire including controller 44 (which may be a computer chip). The single housing can be unitary or it can be made of several pieces, and it can also be jointed, slitted, or otherwise modified to suit particular needs. Although a single housing need not be unitary, it is comprised of physically connected elements so that it can be picked up and carried by a person or other user as a single unit.

Figure 5:
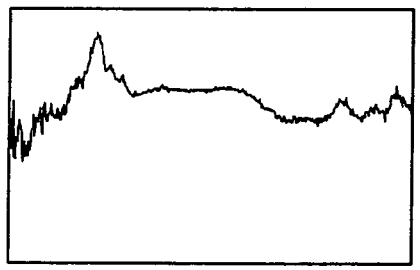
FIG. 5 is a graphical representation of an example of selecting a desired wavelength and intensity distribution.
Figure 5:
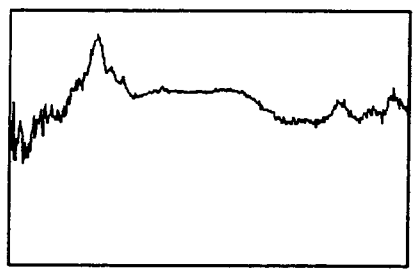
Figure 5:
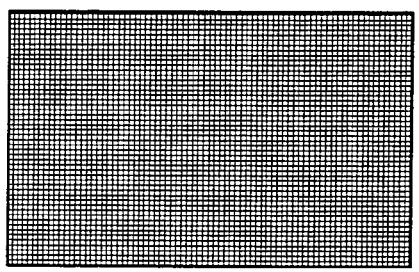
Figure 5:
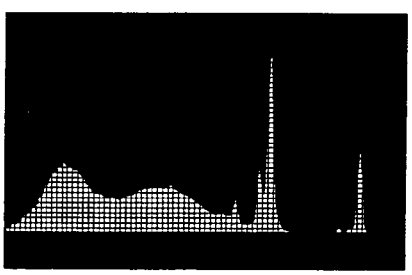
Figure 5:
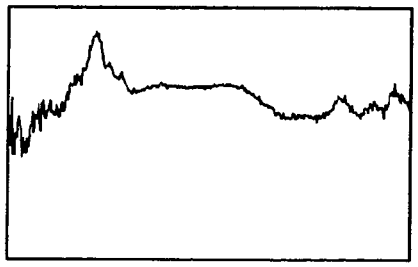
Figure 5:
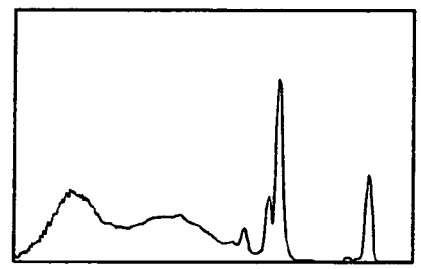

FIG. 5 graphically depicts an example where apparatus and methods as described herein are used to provide no spectral conditioning, or to provide a modified light beam consisting essentially of a selected spectral output and a selected wavelength depended intensity distribution. In case 1 in FIG. 5, light from a xenon light source is reflected off a reflective pixelated SLM wherein all the mirrors are in the "on" state, and thus the output light is substantially identical to the input light. In case 2, the light from the xenon light source is reflected off a reflective pixelated SLM wherein the on/off pattern of the pixels is set to substantially mimic a spectral output of a white Cathode Ray Tube (CRT) display monitor. Accordingly, the output light of the system is also substantially identical to the white CRT pattern. As noted elsewhere herein, alternative patterns can be provided in rapid and simple form as desired.

Turning to some of the methods, and as discussed elsewhere herein, the methods include lighting a scene by directing a light beam along a light path through a spectrum former, and then reflecting the spectrum off a reflective pixelated SLM wherein the reflected light is reflected in a first reflected light path or in at least one second reflected light path that is not back to the spectrum former. This provides a modified light beam comprising a selected spectral output and a selected wavelength dependant intensity distribution.

The methods can further comprise emitting the light beam from a desired light source and switching the modified light beam between one or more reflected light paths. The modified light beam can be passed by a second spatial light modulator, preferably reflected off a second reflective pixelated spatial light modulator, to provide a substantially improved modified light beam. The methods can additionally comprise passing the light beam by a variety of alternate optical elements as discussed herein, such as collimating lenses, collimating mirrors, dichroic mirrors, focusing lenses and projection assemblies. The methods further comprise algorithms wherein a desired or known illumination scenario is encoded in computer-implemented programming, and then the computer-implemented programming controls the on/off pattern of pixels in the reflective pixelated SLM to provide the desired illumination. The programming can control both the wavelengths that are provided and the intensity of the wavelengths, thus providing precise control of both color, and intensity, sometimes referred to as gray scale, of the various components of the illumination. The methods can be applied in lighting systems that are either stand-alone, such as luminaires, or they are a part of other devices, such as lighting systems and scientific apparatus or in movie projectors.

Turning to some additional general discussion, since the light has been spectrally dispersed across the reflective pixelated SLM, selectively turning on or off individual mirror elements can selectively reflect only one narrow wavelength of light from the light dispersive element, such as only a pure green line of light in a typical linear spectrum. Non-linear spectra can also be used; if desired, the entirety or any desired portion of the light can be transmitted to a detector, which detector can then determine the wavelength striking the various detection elements of the detector, and then provide feedback to the reflective pixelated SLM so that only desired pixels are turned on, which set of pixels can be as complex a shape as desired or needed. By varying the duty cycle of certain mirrors in the group to be turned on or off, virtually any spectral distribution of light can be created.

The color control system or detector can include a color responsive feedback element such as a photodiode array or other suitable transducer, that is placed in the path of the spectral image projected toward the reflective pixelated SLM and near to the reflective pixelated SLM image. The color control system can measure beam color distribution of the lamp prior to or after color selection. The color control system may be placed such that it samples either a portion of the beam that does not strike the reflective pixelated SLM. In one embodiment the measurement element can be placed in the path of the light that is not propagated toward the projection optics and the reflective pixelated SLM device can select light to be propagated to the measurement device in response to system controller signals. This provides feed back signals to the controller of the reflective dixelated SLM to allow correction for lot to lot variation and aging among lamps. This can be used to color match among luminaires.

While reflective pixelated SLMs can exhibit high reflectance and can have a signal to noise ratio of about 1000:1, this may not be sufficient for some applications. In some embodiments a second reflective pixelated SLM element can added to the optical path. The selected light from the first reflective pixelated SLM is directed to a second reflective pixelated SLM. Mirrors on the second reflective pixelated SLM illuminated by the selected light direct it to the collection optical path. The other mirrors remain in the "off" position, further attenuating the out of band light. While the desired output light will be further attenuated by a percentage of about 10–90%, the out of band light will be attenuated by a further factor of 1000, which results in a net increase of the signal to noise ratio.

A lamp is a one type of light source that produces optical energy in the form of light by conversion of electrical or chemical energy. Common types of lamps are tungsten filament lamps (Osram-Sylvania) and Quartz-Tungsten-Halogen (QTH) lamps (Gilway Technical Lamp). Preferred sources of illumination have a broad range of energy that is relatively evenly distributed in the visible spectrum. A preferred lamp is a short arc xenon lamp with integral reflector such as the Cermax lamp produced by Perkin Elmer. The invention may employ any type of light emitting object as a light source, providing it encompasses all the wavelengths desired after spectral conditioning.

The output of the lamp can focused, spatially mixed, imaged, collimated, spectrally recombined, and projected. The focusing, collimating, spatial mixing, spectrally recombined, or imaging elements can be lenses, mirrors or other elements as desired, and can be placed between the light source and the wavelength dispersive element or elsewhere in the optical path as desired in view of the present disclosure. The wavelength dispersive element spatially disperses the light from the lamp according to energy or wavelength. Light mixing or recombining systems can comprise a Lambertian diffuser such as a ground or etched glass. Lambertian diffusers may be transmissive or reflective and are available from companies such as Melles-Griot or Labsphere. Light mixing or recombining systems can also comprise a directional light diffuser, which is a diffusing element that scatters light in a directional manner such that the light propagates in a desired direction from the diffuser. One example of a directional light diffuser is a holographic diffuser. A holographic diffuser is a structured optical element created by holography that can spatially homogenize a beam of light. Holographic diffusers can be designed to achieve specific forward scattering angles of light. Holographic diffusers are available from companies such as Physical Optics Corporation of California. Light mixing systems can also comprise a lenslet array. A lenslet array comprises a multiple number of lenses molded or otherwise formed in an optical element in the form of an array that is closely packed together. The array of lenses may be rectangular or hexagonal, fractal or another periodic arrangement of lenses that causes a beam of light to be directed in a way that spatially homogenizes the light energies in the beam. Another suitable light mixing system can comprise a light pipe, which can be rectangular in cross-section and may be tapered or not in the direction of light propagation. The light pipe can be made of a transmissive material such as an optical glass with a refractive index that differs from the medium in which the light pipe is placed, such as air or water, such that total internal reflection of the desired wavelengths occurs. Alternatively, the light pipe can have a box-like arrangement of mirrors open at opposite ends that allows light to propagate by reflection from the mirrored surface along the axis of the box. Light pipes are typically employed in devices such as digital image projectors. The various elements can also be combined, for example a holographic diffuser and light pipe, or a lenslet array and light pipe. The light pipe may have the diffuser or lenslet array embossed, molded, etched, or cemented on one end of it.

The light path(s) can comprise transmission via an optical fiber or optical fiber bundle or other desired light guide. A "light guide" is a device well known in the art, typically flexible, that comprises an outer layer and a light transmissive core that carries light from one location to another, such as an optical fiber, liquid light guide or hollow reflective light guide. The outer layer can comprise the outer surface of the same material that makes up the core or can be a separate or additional material. A light guide typically also comprises a substantially non-light transmissive cladding. A "light guide bundle" is a plurality of such light guides combined into a single strand, and can comprise a binder or filler material between the individual light guides of the bundle. Such cladding and filler, as well as anything else that may be disposed between the light guide cores of a light guide bundle, can be referred to as an inter-core area.

The ability to precisely select wavelengths for illumination is also useful for diagnosing and treating clinical conditions in humans or animals. Light with an action spectrum that activates a drug used for photodynamic therapy can be selected with high precision and may be used in place of some costly light sources such as lasers for some applications. The ability to switch between various wavelengths and to precisely control the amount of light delivered enables a wide range of treatments from a single source.

The ability to precisely select wavelengths for illumination is also useful for enhancing the contrast of a desired object in a scene. Such a light source can be used to enhance the detection of an object by direct human visual inspection, or by using an imaging device such as a camera. Light with a spectrum that enhances contrast may be used in military applications to improve contrast between enemy camouflage and background, or to assist in identifying friend and foe. It could also be used to enhance detection of survivors for air-sea rescue, discrimination between types of vegetation, or other objects of interest.

From the foregoing, it will be appreciated that, although specific embodiments of the invention have been described herein for purposes of illustration, various modifications may be made without deviating from the spirit and scope of the invention. Accordingly, the invention includes such modifications as well as all permutations and combinations of the subject matter set forth herein and is not limited except as by the appended claims.

What is claimed is:

1. A lighting system that provides a variable selected spectral output and a variable wavelength dependent intensity distribution, the lighting system comprising a light path that comprises:

a) a spectrum former configured to provide a spectrum from a light beam traveling along the light path, and b) a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light comprising the desired spectral and intensity distribution, the desired segment of light consisting essentially of a desired selected spectral output and a desired wavelength dependent intensity distribution, c) and wherein the pixelated spatial light modulator is a first pixelated spatial light modulator, and wherein the desired segment of light is directed to a second spatial light modulator operably connected to at least one controller containing computer-implemented programming that controls an on/off pattern of pixels in the second spatial light modulator to select the desired segment.

2. The lighting system of claim 1 wherein the first pixelated spatial light modulator and the second pixelated spatial light modulator are connected to a single controller.

3. The lighting system of claim 1 wherein the desired selected spectral output and desired wavelength dependent intensity distribution substantially mimic a desired portion of a wavelength dependent distribution of output energy of at least one of a known lamp, a cathode ray tube image display device, a light emissive image display device and a source of optical radiation.

4. The lighting system of claim 1 wherein the desired selected spectral output and desired wavelength dependent intensity distribution substantially mimic a desired wavelength dependent distribution of output energy corresponding to a desired natural ambient lighting scenario.

5. The lighting system of claim 1 wherein the desired selected spectral output and desired wavelength dependent intensity distribution substantially mimic a desired wavelength dependent distribution of output energy for disease treatment.

6. The lighting system of claim 1 wherein the desired selected spectral output and desired wavelength dependent intensity distribution substantially mimic a desired wavelength dependent distribution of output energy for photodynamic therapy.

7. The lighting system of claim 1 wherein the desired selected spectral output and desired wavelength dependent intensity distribution substantially mimic a desired wavelength dependent distribution of output energy for disease diagnosis.

8. The lighting system of claim 1 wherein the desired segment is selected to substantially mimic a spectral output and a wavelength dependent intensity distribution of output energy that can enhance contrast for detection or discrimination of a desired object in a scene.

9. The lighting system of claim 1 wherein the lighting system further comprises a heat removal element operably connected to the light source to remove undesired energy emitted from the light source toward at least one of the reflective pixelated spatial light modulator, the optical element, and the spectrum former.

10. A lighting system that provides a variable selected spectral output and wavelength dependent intensity distribution, the lighting system comprising a light path that comprises:
  a) a spectrum former configured to provide a spectrum from a light beam traveling along the light path, and
  b) a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light comprising the desired spectral and intensity distribution, the desired segment of light consisting essentially of a desired selected spectral output and a desired wavelength dependent intensity distribution, and
  c) a detector operably connected to a controller containing computer-implemented programming configured to determine from the detector whether the desired segment contains a desired selected spectral output and a desired wavelength dependent intensity distribution, and adjust the on/off pattern of pixels in the pixelated spatial light modulator to improve the correspondence between the desired segment and the desired selected spectral output and the desired wavelength dependent intensity distribution.

11. The lighting system of claim 10 wherein the system further comprises a light source located upstream from the spectrum former.

12. The lighting system of claim 10 wherein the pixelated spatial light modulator is a first pixelated spatial light modulator, and wherein the desired segment of light is directed to a second pixelated spatial light modulator operably connected to at least one controller containing computer-implemented programming that controls the on/off pattern of pixels in the second spatial light modulator to select the desired segment.

13. The lighting system of claim 10 wherein the system further comprises an optical projection device located downstream from at least one of the first pixelated spatial light modulator and the second pixelated spatial light modulator to project light as a directed light beam.

14. The lighting system of claim 10 wherein the desired selected spectral output and desired wavelength dependent intensity distribution substantially mimic a desired portion of a wavelength dependent distribution of output energy of at least one of a known lamp, a cathode ray tube image display device, a light emissive image display device and a source of optical radiation.

15. The lighting system of claim 10 wherein the desired selected spectral output and desired wavelength dependent intensity distribution substantially mimic a desired wavelength dependent distribution of output energy corresponding to a desired natural ambient lighting scenario.

16. The lighting system of claim 10 wherein the desired selected spectral output and desired wavelength dependent intensity distribution substantially mimic a desired wavelength dependent distribution of output energy for disease treatment.

17. The lighting system of claim 10 wherein the desired selected spectral output and desired wavelength dependent intensity distribution substantially mimic a desired wavelength dependent distribution of output energy for photodynamic therapy.

18. The lighting system of claim 10 wherein the desired selected spectral output and desired wavelength dependent intensity distribution substantially mimic a desired wavelength dependent distribution of output energy for disease diagnosis.

19. The lighting system of claim 10 wherein the desired segment is selected to substantially mimic a spectral output and a wavelength dependent intensity distribution of output energy that can enhance contrast for detection or discrimination of a desired object in a scene.

20. The lighting system of claim 10 wherein the lighting system further comprises a heat removal element operably connected to the light source to remove undesired energy emitted from the light source toward at least one of the reflective pixelated spatial light modulator, the optical element, and the spectrum former.

21. A stand alone luminaire sized to project light onto a scene and having a variable selected spectral output and wavelength dependent intensity distribution, the luminaire comprising:
  a) a high output light source,
  b) a spectrum former optically connected to and downstream from the light source to provide a spectrum from a light beam emitted from the light source,
  c) a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light comprising the desired spectral and intensity distribution, the desired segment of light consisting essentially of a desired selected spectral output and a desired wavelength dependent intensity distribution, d) a projection system optically connected to and downstream from the pixelated spatial light modulator in the first direction, wherein the projection system projects the desired segment as a directed light beam to illuminate the scene, and e) a detector optically connected to and downstream from the pixelated spatial light modulator, the detector also operably connected to a controller containing computer-implemented programming configured to determine from the detector whether the desired segment contains a desired selected spectral output and a desired wavelength dependent intensity distribution, and adjust the on/off pattern of pixels in the pixelated spatial light modulator to improve the correspondence between the desired segment and the desired selected spectral output and the desired wavelength dependent intensity distribution.

22. The luminaire of claim 21 wherein the pixelated spatial light modulator is a first pixelated spatial light modulator, and wherein the desired segment of light is directed to a second spatial light modulator operably connected to at least one controller containing computer-implemented programming that controls an on/off pattern of pixels in the second pixelated spatial light modulator to provide an improved desired selected spectral output and desired wavelength dependent intensity distribution in the desired segment of light.

23. The luminaire of claim 21 wherein the desired selected spectral output and desired wavelength dependent intensity distribution substantially mimic a desired portion of a wavelength dependent distribution of output energy of at least one of a known lamp, a cathode ray tube image display device, a light emissive image display device and a source of optical radiation.

24. The luminaire of claim 21 wherein the desired selected spectral output and desired wavelength dependent intensity distribution substantially mimic a desired wavelength dependent distribution of output energy corresponding to a desired natural ambient lighting scenario.

25. The luminaire of claim 21 wherein the desired selected spectral output and desired wavelength dependent intensity distribution substantially mimic a desired wavelength dependent distribution of output energy for disease treatment.

26. The luminaire of claim 21 wherein the desired selected spectral output and desired wavelength dependent intensity distribution substantially mimic a desired wavelength dependent distribution of output energy for photodynamic therapy.

27. The luminaire of claim 21 wherein the desired selected spectral output and desired wavelength dependent intensity distribution substantially mimic a desired wavelength dependent distribution of output energy for disease diagnosis.

28. The luminaire of claim 21 wherein the desired segment is selected to substantially mimic a spectral output and a wavelength dependent intensity distribution of output energy that can enhance contrast for detection or discrimination of a desired object in a scene.

29. The luminaire of claim 21 wherein the luminaire further comprises a heat removal element operably connected to the light source to remove undesired energy emitted from the light source toward at least one of the reflective pixelated spatial light modulator, the optical element, and the spectrum former.

30. The luminaire of claim 21 wherein the system further comprises a spectral recombiner optically connected to and located downstream from the pixelated spatial light modulator.

31. The luminaire of claim 21 wherein the detector comprises at least one of a CCD, a CID, a CMOS, and photodiode array.

32. The luminaire of claim 22 wherein the high output light source, the spectrum former, the optical element that provides an enhanced image, the pixelated spatial light modulator, and the projection system, are all located in a single housing.

33. A method of lighting a scene comprising:

a) directing a light beam along a light path and through a spectrum former to provide a spectrum from the light beam traveling;

b) passing the spectrum by a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light consisting essentially of a desired selected spectral output and a desired wavelength dependent intensity distribution, c) transmitting the desired segment of light to a detector operably connected to a controller containing computer-implemented programming configured to determine from the detector whether the desired segment contains the desired selected spectral output and a desired wavelength dependent intensity distribution, and adjusting the on/off pattern of pixels in the pixelated spatial light modulator to improve the correspondence between the desired segment and the desired selected spectral output and the desired wavelength dependent intensity distribution.

34. The method of claim 33 wherein the method further comprises emitting the light beam from a light source located in a same housing as and upstream from the spectrum former, and wherein the spectrum former comprises at least one of a prism and a diffraction grating.

35. The method of claim 33 wherein the method further comprises passing the light beam by an optical element between the spectrum former and the pixelated spatial light modulator to provide a substantially enhanced image of the spectrum from the spectrum former to the pixelated spatial light modulator.

36. The method of claim 33 wherein the pixelated spatial light modulator is a first pixelated spatial light modulator, and wherein the method further comprises passing the modified light beam by a second reflective spatial light modulator operably connected to at least one controller containing computer-implemented programming that controls an on/off pattern of pixels in the second pixelated spatial light modulator to select the desired segment of light.

37. The method of claim 33 wherein the method further comprises passing the modified light beam by an optical projection device located downstream from the pixelated spatial light modulator to project light as a directed light beam.

38. The method of claim 33 wherein the desired segment is selected to substantially mimic a spectral output and a wavelength dependent intensity distribution of at least one of a known lamp, a cathode ray tube image display device, a light emissive image display device and a source of optical radiation.

39. The method of claim 33 wherein the desired segment is selected to substantially mimic a spectral output and a wavelength dependent intensity distribution of output energy corresponding to a desired natural ambient lighting scenario.

40. The method of claim 33 wherein the desired segment is selected to substantially mimic a spectral output and a wavelength dependent intensity distribution of output energy for disease treatment.

41. The method of claim 33 wherein the desired segment is selected to substantially mimic a spectral output and a wavelength dependent intensity distribution of output energy for photodynamic therapy.

42. The method of claim 33 wherein the desired segment is selected to substantially mimic a spectral output and a wavelength dependent intensity distribution of output energy for disease diagnosis.

43. The method of claim 33 wherein the pixelated spatial light modulator is a digital micromirror device.

44. A method of lighting a scene comprising:
 a) directing a light beam along a light path and through a spectrum former to provide a spectrum from the light beam traveling; and,
 b) passing the spectrum by a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light consisting essentially of a desired selected spectral output and a desired wavelength dependent intensity distribution,
 c) wherein the pixelated spatial light modulator is a first pixelated spatial light modulator, and wherein light from the first pixelated spatial light modulator is directed to a second spatial light modulator operably connected to at least one controller containing computer-implemented programming that controls an on/off pattern of pixels in the second spatial light modulator to select the desired segment.

45. The method of claim 44 wherein the method further comprises emitting the light beam from a light source located in a same housing as and upstream from the spectrum former, and wherein the spectrum former comprises at least one of a prism and a diffraction grating.

46. The method of claim 45 wherein the method further comprises an optical projection device located downstream from at least one of the first pixelated spatial light modulator and the second pixelated spatial light modulator to project light as a directed light beam.

47. A method of emitting modified light consisting essentially of a desired selected spectral output and a desired wavelength dependent intensity distribution from a stand alone luminaire, the method comprising:
 a) emitting light from a high output light source located in a housing of the luminaire;
 b) passing the light by a spectrum former optically connected to and downstream from the light source to provide a spectrum from a light beam emitted from the light source;
 c) passing the spectrum by an optical element connected to and downstream from the spectrum former to provide an enhanced image of the spectrum;
 d) passing the spectrum by a pixelated spatial light modulator located downstream from and optically connected to the spectrum former, the pixelated spatial light modulator configured to pass desired light from the spectrum to select a segment of light, wherein the pixelated spatial light modulator is operably connected to at least one controller containing computer-implemented programming that controls an on/off pattern of pixels in the pixelated spatial light modulator to provide a desired segment of light consisting essentially of a desired selected spectral output and a desired wavelength dependent intensity distribution,
 e) passing the modified light beam by a projection system optically connected to and downstream from the pixelated spatial light modulator in the first direction, wherein the projection system projects the modified light beam from the luminaire as a directed light beam, and
 f) transmitting the desired segment of light to a detector operably connected to a controller containing computer-implemented programming configured to determine from the detector whether the desired segment contains the desired selected spectral output and a desired wavelength dependent intensity distribution, and adjusting the on/off pattern of pixels in the pixelated spatial light modulator to improve the correspondence between the desired segment and the desired selected spectral output and the desired wavelength dependent intensity distribution.

48. The method of claim 47 wherein the method further comprises adjusting the on/off pattern of pixels in the pixelated spatial light modulator to improve the correspondence between the desired segment and the desired selected spectral output and the desired wavelength dependent intensity distribution.

49. The method of claim 47 or 48 wherein the method further comprises removing undesired energy emitted from the light source toward at least one of the pixelated spatial light modulator, the optical element, and the spectrum former, the removing effected via a heat removal element operably connected to the light source.

50. The method of claim 47 wherein the pixelated spatial light modulator is a first pixelated spatial light modulator, and wherein the desired segment is directed to a second spatial light modulator operably connected to at least one controller containing computer-implemented programming that controls an on/off pattern of pixels in the second pixelated spatial light modulator to provide an improved desired selected spectral output and desired wavelength dependent intensity distribution.

51. The method of claim 47 or 48 wherein the desired selected spectral output and desired wavelength dependent intensity distribution substantially mimic a desired portion of a wavelength dependent distribution of output energy of at least one of a known lamp, a cathode ray tube image display device, a light emissive image display device and a source of optical radiation.

52. The method of claim 47 or 48 wherein the desired selected spectral output and desired wavelength dependent intensity distribution substantially mimic a desired wavelength dependent distribution of output energy corresponding to a desired natural ambient lighting scenario.

53. The method of claim 47 or 48 wherein the desired selected spectral output and desired wavelength dependent intensity distribution substantially mimic a desired wavelength dependent distribution of output energy for disease treatment.

54. The method of claim 47 or 48 wherein the desired selected spectral output and desired wavelength dependent intensity distribution substantially mimic a desired wavelength dependent distribution of output energy for photodynamic therapy.

55. The method of claim 47 or 48 wherein the desired selected spectral output and desired wavelength dependent intensity distribution substantially mimic a desired wavelength dependent distribution of output energy for disease diagnosis.

56. The method of claim 47 or 48 wherein the method further comprises passing the desired segment by a spectral recombiner optically connected to and located downstream from the pixelated spatial light modulator.

* * * * *